(12) United States Patent
Westhaver et al.

(10) Patent No.: US 6,669,705 B2
(45) Date of Patent: Dec. 30, 2003

(54) APPARATUS AND METHOD FOR WELDING SUTURES

(75) Inventors: Paul A. Westhaver, Newburyport, MA (US); John V. Yannone, Seabrook, NH (US)

(73) Assignee: Axya Medical, Inc., Beverly, MA (US)

( * ) Notice: Subject to any disclaimer, the term of this patent is extended or adjusted under 35 U.S.C. 154(b) by 56 days.

(21) Appl. No.: 09/859,985

(22) Filed: May 17, 2001

(65) Prior Publication Data

US 2002/0035371 A1 Mar. 21, 2002

Related U.S. Application Data

(60) Provisional application No. 60/264,912, filed on Jan. 29, 2001, and provisional application No. 60/204,975, filed on May 17, 2000.

(51) Int. Cl.[7] ......................... A61B 17/10; A61B 17/04
(52) U.S. Cl. ....................... 606/139; 606/148
(58) Field of Search ............... 606/228, 232, 606/148, 139, 113, 27, 28, 29, 30, 40, 41, 42, 46, 49, 51, 52, 151, 142, 143, 205, 206, 207, 208; 227/91

(56) References Cited

U.S. PATENT DOCUMENTS

| | | | |
|---|---|---|---|
| 5,306,280 A | * | 4/1994 | Bregen et al. ............... 227/901 |
| 5,746,757 A | * | 5/1998 | McGuire .................... 606/139 |
| 5,865,835 A | | 2/1999 | Lolagne |
| 5,893,880 A | | 4/1999 | Egan et al. ................. 606/228 |
| 6,010,516 A | * | 1/2000 | Hulka ........................ 606/148 |
| 6,077,277 A | * | 6/2000 | Mollenauer et al. ........ 606/139 |

* cited by examiner

*Primary Examiner*—Kevin Shaver
*Assistant Examiner*—Candice C. Melson
(74) *Attorney, Agent, or Firm*—McDermott, Will & Emery (57) ABSTRACT

The present invention provides an apparatus and a method for welding sutures. The apparatus comprises a jaw assembly and a heater element. The jaw assembly includes a first jaw for receiving a first suture segment, and a second jaw for receiving a second suture segment such that the first and the second suture segments overlap. The heater element is positionable and retractable along an axis between the jaws, and is adapted to be positioned between and melt at least opposing surfaces of the overlapping first and second suture segments so that the suture segments can be pressed together and bonded. The method of welding suture segments includes positioning suture segments adjacent to and on opposite sides of a heater element, energizing the heater element such that portions of the suture segments in contact with the heater element melt, withdrawing the heater element, and clamping the suture segments together until the melted portions cool.

62 Claims, 5 Drawing Sheets

APPARATUS AND METHOD FOR WELDING SUTURES

CROSS REFERENCE TO RELATED APPLICATION

The present application claims priority from co-pending provisional U.S. patent application Ser. No. 60/204,975, filed May 17, 2000, and co-pending provisional U.S. Patent Application Ser. No. 60/264,912, filed Jan. 29, 2001, both of which are incorporated herein by reference in their entireties.

FIELD OF THE DISCLOSURE

The present disclosure relates to improvements in sutures and suturing techniques, and more particularly to a welder and method of welding for making high-strength fused suture loops during endoscopic surgical procedures.

BACKGROUND OF THE DISCLOSURE

In surgical procedures, a suture is typically used to stitch or secure the edges of tissue together to maintain them in proximity until healing is substantially completed. The suture is generally directed through the portions of the tissue to be joined and formed into a single loop or stitch, which is then knotted in order to maintain the wound edges in the appropriate relationship to each other for healing to occur. In this manner, a series of stitches of substantially uniform tension can be made in tissue. Because the stitches are individual and separate, the removal of one stitch does not require removal of them all or cause the remaining stitches to loosen. However, each individual stitch requires an individual knot or some other stitch-closing device for securing the stitch around the wound.

It is sometimes necessary or desirable to close a wound site with sutures without having to form knots or incorporate loop-closing devices in the sutures, such as, for example, in surgical repair of delicate organs or tissues, where the repair site is relatively small or restricted. Apparatuses and methods for fusing suture loops have therefore also been provided. A fused suture loop must provide the appropriate tension on the wound edges and the appropriate strength to maintain the wound edges in sufficient proximity for a sufficient time to allow healing to occur.

Polymer sutures are particularly amenable to various fusing or joining processes, such as, for example, welding, whereby sections of the sutures can be fused together upon application of sufficient heat to the sections to cause partial melting and fusion of the sections. U.S. Pat. No. 5,893,880, for example, discloses a fused loop of an elongated material, such as a surgical suture, and apparatus for making the loop. Portions of one or more segments to be joined together are fused in a welding process to form a welded joint. The shear area of the fused portion of the joint determines the strength of the joint and is thus preferably relatively large. Various configurations for the welding apparatus facilitate the creation of relatively large fused portions of the joint by maximizing contact between at least one of the welding members of the apparatus and at least one of the segments to be joined.

What is still desired is an apparatus and a method of welding sutures so that high-strength fused suture loops are provided. Preferably, the apparatus and method will provide for ease of suture management before, after and during welding of the suture. In addition, the apparatus and method will preferably allow endoscopic suture welding. Futhermore, it is desired that the apparatus and method will provide a fused loop of an elongated material, such as a polymeric suture material, which has a strength in the joint region which is at least equal to, if not greater than, the strength of the parent material.

SUMMARY OF THE DISCLOSURE

The present disclosure, accordingly, provides an apparatus and method for creating a fused loop of an elongated material, such as a polymeric suture material. The apparatus comprises a suture welder including a jaw assembly and a heater element. The jaw assembly includes a first jaw for receiving a first suture segment, and a second jaw for receiving a second suture segment so that the second suture segment is adjacent the first suture segment. The heater element is positioned relative to the jaws, and is adapted to be positioned between and melt at least adjacent surfaces of the overlapping first and second suture segments so that the suture segments can be pressed together and bonded.

The present disclosure also provides a method of welding suture segments. The method includes positioning suture segments adjacent to and on opposite sides of a heater element, and energizing the heater element such that portions of the suture segments in contact with the heater element melt. The method also includes clamping the suture segments together until the melted portions cool, resulting in an inter-segment bond, and then releasing the bonded suture segments.

These and other features of the present disclosure will be more fully appreciated with reference to the following detailed description which is to be read in conjunction with the attached drawings.

BRIEF DESCRIPTION OF THE DRAWINGS

The disclosure is further described by the following description and figures, in which.

DETAILED DESCRIPTION OF THE DISCLOSURE

Referring first to FIGS. 1 through 8, the present disclosure provides a suture welder 10 for creating a fused loop 14 of an elongated material, such as a polymeric suture material 16. The suture welder 10 includes a jaw assembly 18 having a first jaw 20 for receiving a first suture segment 22, and a second jaw 24 for receiving a second suture segment 26 so that the second suture segment is adjacent the first suture segment. The suture welder 10 also includes a heater element 12 positioned between the suture segments 22, 26. The heater element 12 is adapted to melt at least adjacent surfaces of the overlapping first and second suture segments 22, 26. Once melted, the suture segments 22, 26 can be pressed together by the jaws 20, 24 and allowed to cool to form a fused layer 28 to secure the suture segments 22, 26 together.

The suture welder 10 of the present disclosure beneficially provides a fused loop 14 of an elongated material, such as a surgical suture 16, wherein the loop has at least comparable strength to knotted loops or loops closed by other means. The fused loop 14 gains its comparable strength from the properties of the fused layer 28 of the loop, as detailed more fully in U.S. Pat. No. 5,893,880, which is assigned to the assignee of the present disclosure and incorporated herein by reference.

Figure 4:
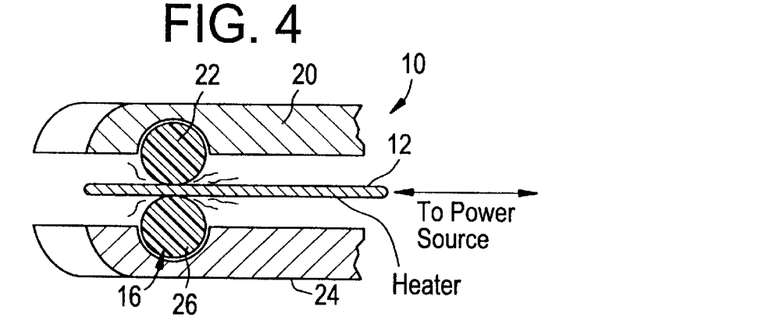
FIGS. 4 through 8 are cross-sectional views showing the suture welder of FIG. 2 clamping, heating, bonding and releasing the two suture segments.
Figure 5:
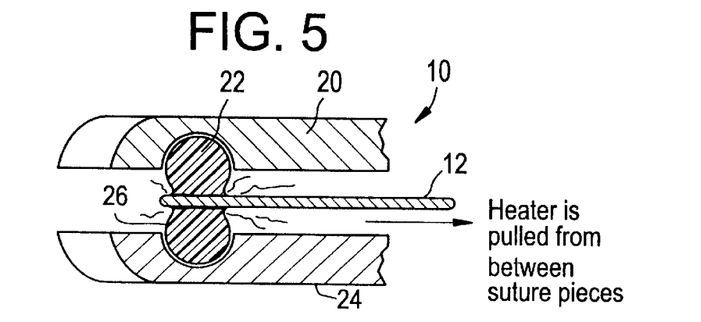
Figure 6:
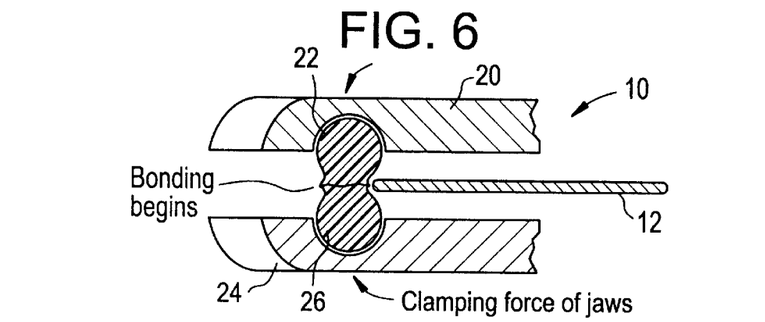
Figure 7:
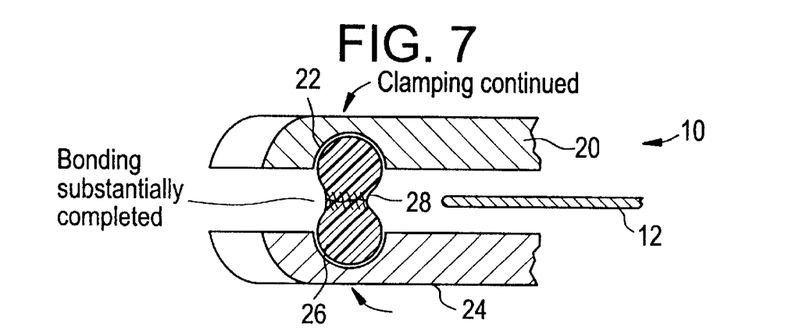
Figure 8:
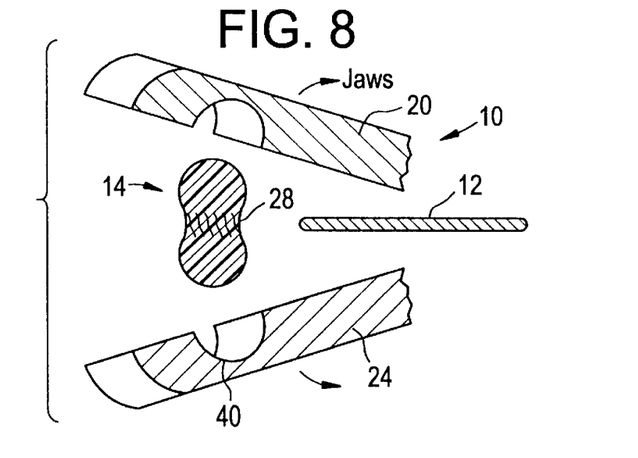
Figure 9:
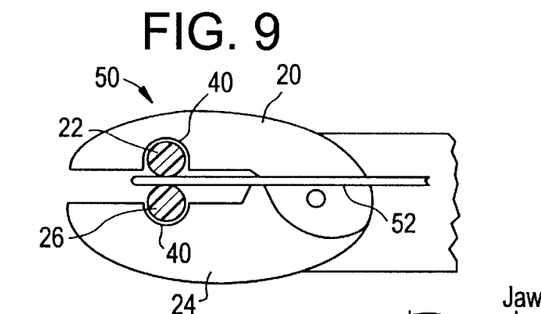
FIG. 9 is an enlarged perspective view of another suture welder according to the present disclosure for use with the assembly of FIG. 1, and shown holding two suture segments.
Figure 10:
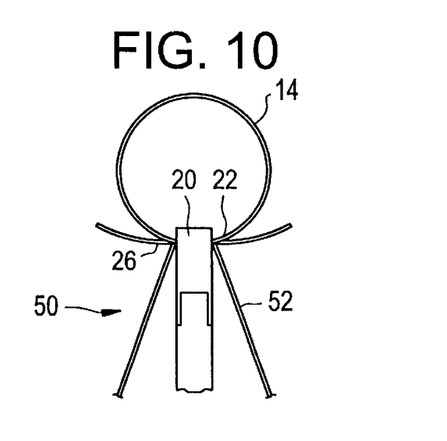
FIG. 10 is a top plan view of the suture welder of FIG. 9 shown holding the two suture segments.
Figure 11:
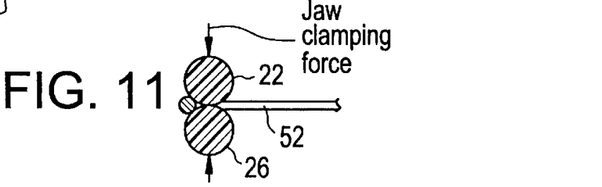
FIGS. 11 through 14 are cross-sectional views showing the suture welder of FIG. 9 clamping, heating, bonding and releasing the two suture segments.
Figure 12:
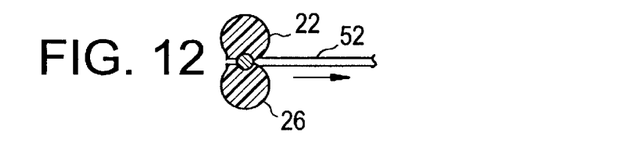
Figure 13:
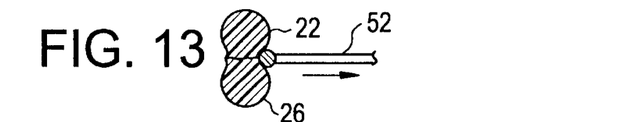
Figure 14:
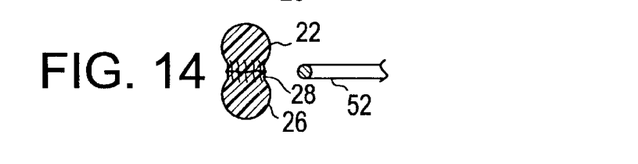
Figure 15:
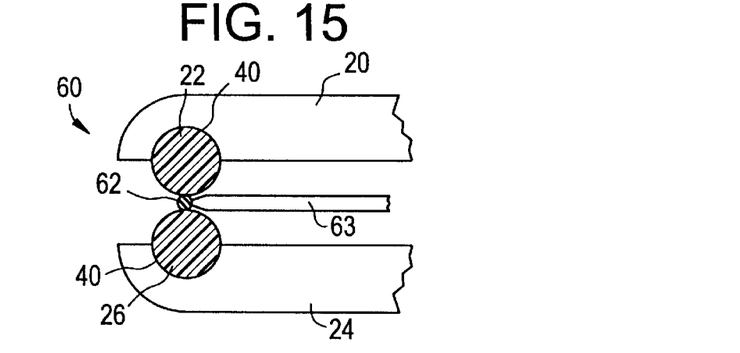
FIG. 15 is a cross-sectional view of an additional suture welder according to the present disclosure for use with the assembly of FIG. 1, and shown holding two suture segments.
Figure 16:
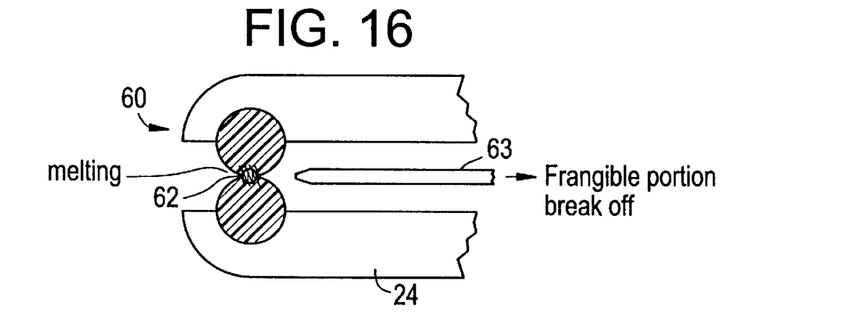
FIGS. 16 through 19 are cross-sectional views showing the suture welder of FIG. 15 clamping, heating, bonding and releasing the two suture segments.
Figure 17:
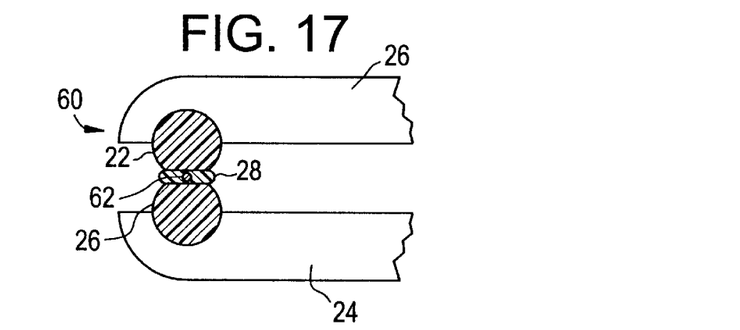
Figure 18:
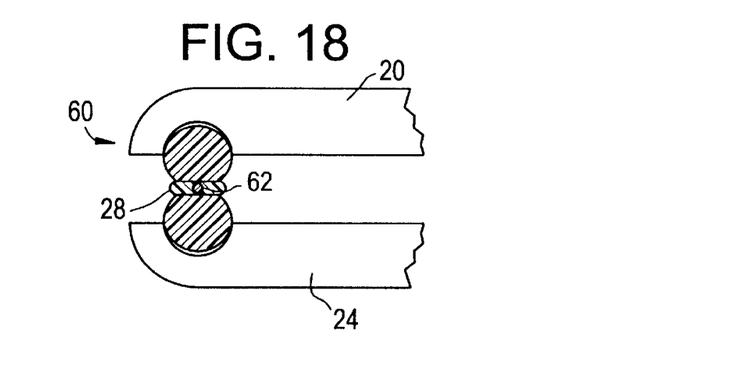
Figure 19:
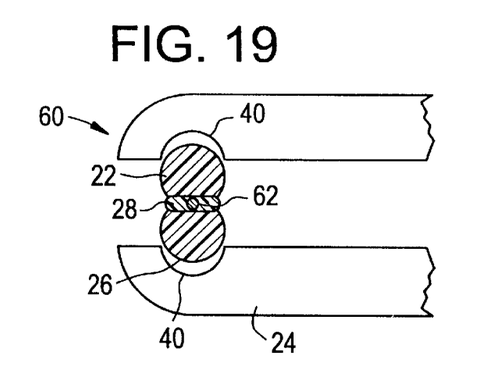

In particular, the fused loop 14 is formed through a welding process in which portions of the suture segments 22, 26 are locally heated through the application of heat thereto until opposing portions melt, as shown in FIGS. 4 and 5. The melted portions are then pressed together in an overlapped joint, as shown in FIG. 6, and become fused, as shown in FIGS. 7 and 8. The joint includes a fused layer 28 between and joining the first and second suture segments 22, 26. The fused layer 28 is fused material from the first and second suture segments 22, 26 and preferably is relatively thin and has a relatively large shear area compared to the suture segments 22, 26. The suture welder 10 facilitates the creation of such a fused portion by maximizing contact between the suture segments 22, 26 during welding.

The fused loop 14 produced by the suture welder 10 comprises one or more pieces of an elongated material, such as a surgical suture, or other material which is amenable to bonding through the application of heat thereto. Suitable materials for the elongated material include polymers, especially thermoplastic materials such as, for example, nylon (polyamide), polypropylene, DACRON® (polyester), polyglycolic acid (PGA), polyglyconate, and polydioxanone. The elongated material 16 can be made of a single strand of a substantially monofilamentous material, or it can comprise multiple strands forming a single suture. The multi-strands can be twisted, braided or otherwise interlinked to increase the density, and thus the strength, of the composite strand.

Figure 1:
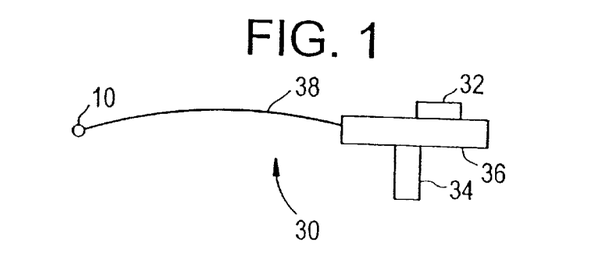
FIG. 1 is a schematic illustration of an endoscopic suture welder assembly constructed in accordance with the present disclosure.

Referring to FIG. 1, the suture welder 10 is preferably for use as part of an endoscopic assembly 30, further including a battery case 32, a handle 34 and a controller 36 remotely connected through a stem 38 to the suture welder 10. The assembly 30 allows the suture welder 10 to be inserted into a patient's body and be controlled from outside the body through the handle 34 and the controller 36. Preferably, at least one or more elements of the endoscopic assembly 30, and possibly the entire assembly, will be provided in a sterilized container and be disposable after a single use. For example, the suture welder 10 and the stem 38 are preferably removably attached to the endoscopic assembly, and are adapted to be disposable after a single medical procedure including multiple fusings of suture loops, or be disposable after fusing a single suture loop.

Referring to FIGS. 2 through 8, preferably the jaws 20, 24 are made of a low friction material, such as TEFLON®, and include suture grooves 40 for receiving and correctly positioning the suture segments 22, 26. Alternatively, the jaws 20, 24 can be made of another material, such as metal, with a low friction material lining the grooves 40. The jaws 20, 24 are arranged (e.g., hinged or pivotally connected together) so that they can be opened and closed in a conventional manner. The jaw assembly 18 includes conventional automatic or manually-operated mechanism(s) for biasing the jaws 20, 24 together.

The heater element 12, which in the particular embodiment shown comprises an electrical resistance heater element in the form of a thin film 12 made of an alloy of nickel, chromium and iron, such as NICHROME®, is also coated with a low friction material, such as KAPTON® polyamide film. The suture welder 10, therefore, has excellent suture management attributes which allow suture segments 22, 26 to be easily and correctly positioned for welding.

It should be understood that the heater element 12 is not meant to be limited to an embodiment that creates heat from electrical energy. Other types of heater elements can alternatively be used, such as a heater element that creates heat by induction, irradiation or a chemical reaction, for example. In addition, the heater element 12 can be made of any suitable material, such as metal, plastic or ceramic. Furthermore, the surfaces of the heater element can be etched in a predetermined manner to ensure the heater element produces a uniform amount of heat to all portions of the suture segments 22, 26. FIG. 2A shows a suture welder which includes a heater element 12A having an etched surface 13 according to one preferred embodiment of the present invention.

Figure 3:
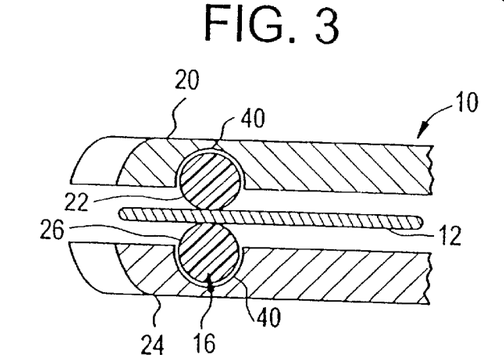
FIG. 3 is a cross-sectional view of the suture welder of FIG. 2 shown holding two suture segments.

Referring to FIGS. 3 through 8, a method of welding according to the present disclosure is shown. First, a surgeon threads the suture segments 22, 26 into the suture grooves 40 of the jaws 20, 24 on opposite sides of the heater element 12, as shown in FIG. 3. Then electrical energy is applied to the resistive heater element 12, such that thermal energy is applied to the opposing surfaces of the suture segments 22, 26, as illustrated in FIG. 4. After either a predetermined time, a predetermined temperature, a combination of both, or some other indicia that a suitable amount of melting of the suture segments 22, 26 has occurred, the thin film heater element 12 is pulled from between the suture segments 22, 26 and the suture segments 22, 26 are biased together with the jaws 20, 24, as shown in FIGS. 5 and 6.

Although not shown, the suture welder 10 includes a release mechanism for releasing the heater element 12 after the predetermined time, temperature, a combination of both, or some other indicia that a suitable amount of melting of the suture segments 22, 26 has occurred, and a withdrawal mechanism that pulls the heater element 12 from between the suture segments 22, 26 upon the release mechanism functioning. The withdrawal mechanism can simply comprise, for example, a compression spring attached between the heater element 12 and the jaw assembly 18. The release mechanism may comprise, for example, a piece of material extending between one of the jaws 20, 24 and the heater element 12 to hold the heater element 12 between the suture segments 22, 26, and wherein the piece of material is temperature sensitive and weakens or breaks upon the heater element 12 reaching a predetermined temperature. Alternatively, the release mechanism can act as a circuit breaker and break upon a predetermined level of electrical power being supplied to the heater element 12. Many alternatives are possible.

Preferably, the jaws 20, 24 are adapted to come together no less than a predetermined minimum distance, so that the suture segments 22, 26 are not "over-compressed". For example, a spacer can be positioned between the jaws 20, 24 to ensure that the bonding suture segments 22, 26 are not over-compressed. Alternatively, a contact-less position sensor can be used to prevent the jaws 20, 24 from over-compressing the suture segments 22, 26. A suitable contact-less position sensor can comprise, for example, a Hall effect cell including a sensor positioned in one of the jaws 20, 24 and a magnetic target positioned in the other of the jaws 20, 24. The Hall effect cell also includes a specific magnetic circuit that directly obtains an output signal whose value varies with the distance separating the jaws 20, 24. In any event, after a suitable bonding period, the jaws 20, 24 are separated and the bonded suture loop 14 is released from the welder 10, as shown in FIG. 8.

Referring to FIGS. 9 through 14, another suture welder 50 constructed in accordance with the present disclosure is shown. The suture welder 50 is similar to the suture welder 10 of FIGS. 2 through 8. The suture welder 50, however, includes a resistance heater element that comprises a thin wire 52 of suitable material, such as an alloy of nickel, chromium and iron, like NICHROME®. The thin heater wire 52 is preferably coated with a low friction material such as KAPTON®polyamide film.

Referring to FIGS. 15 through 19, an additional suture welder 60 according to the present disclosure for use with the assembly 30 of FIG. 1 is shown holding two suture segments 22, 26. The suture welder 60 is similar to the suture welder 10 of FIGS. 2 through 8. The suture welder 60, however, includes a resistance heater element that comprises a thin wire 62 of suitable material, such as an alloy of nickel, chromium and iron, like NICHROME®, and frangible leads 63 extending from the wire 62. The frangible leads 63 act as circuit breakers and break off upon a predetermined level of electrical power being supplied to the heater element 62, thereby leaving the heater element 62 to become encapsulated in the fused layer 28 of the suture segments 22, 26.

Figure 20:
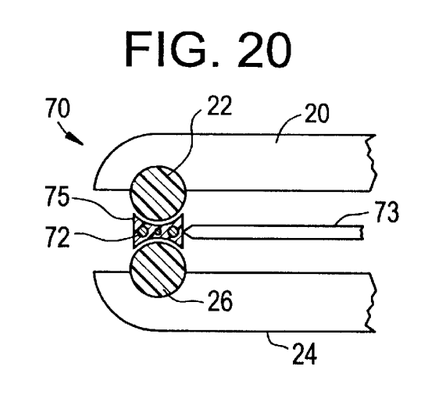
FIGS. 20 and 21 are a cross-sectional views of a further suture welder according to the present disclosure for use with the assembly of FIG. 1, and shown holding two suture segments prior to bonding and releasing the two suture segments after bonding.
Figure 21:
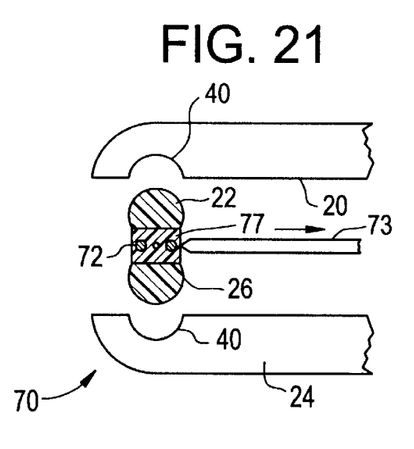

FIGS. 20 and 21 are a cross-sectional views of a further suture welder 70 according to the present disclosure for use with the assembly 30 of FIG. 1, and shown holding two suture segments 22, 26 prior to bonding and releasing the two suture segments 22, 26 after bonding. The suture welder 70 includes a heater element comprising a heating array 72 encapsulated in plastic 75 and connected to frangible leads 73. Upon heating, the array 72 melts the plastic encapsulate 75 and adjacent surfaces of the suture segments 22, 26. The frangible leads 73 break off to leave the heater array 72 within the melted encapsulate 75. The jaws 20, 24 are clamped and the melted encapsulate 75 and adjacent surfaces of the suture segments 22, 26 are allowed to cool and form a fused portion or layer 77 between and joining the first and second suture segments 22, 26.

Figure 2:
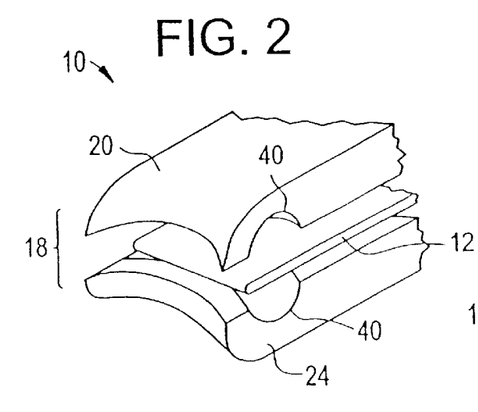
FIG. 2 and FIG. 2A are side elevation views of a suture welder of the assembly of FIG. 1.
Figure 2A:
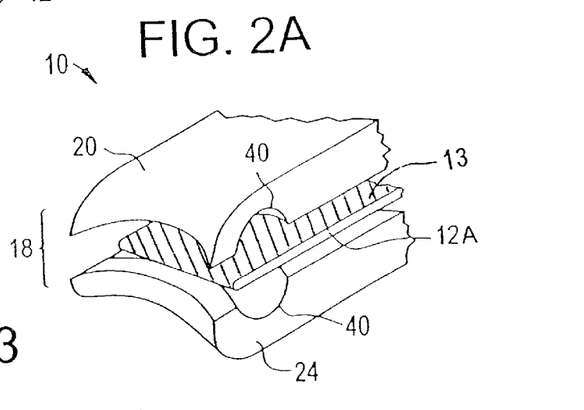
Figure 22:
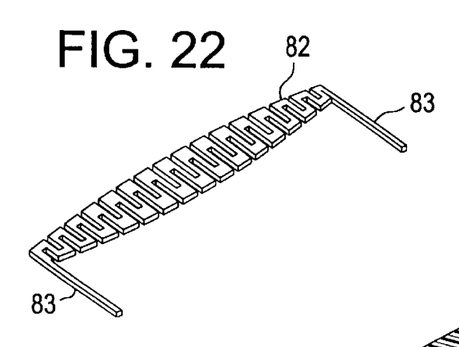
FIG. 22 is a perspective view of a non-uniform heating array for use with a suture welder according to the present disclosure.

FIG. 22 is a perspective view of a non-uniform heating array 82 for use with the suture welder 10 of FIG. 2. The heating array 82 is shaped to deliver heat to the surfaces of the suture segments 22, 26 in a specific pattern. Although a particular shape is shown, the heating array can be provided with any suitable shape for delivering heat to the surfaces of the suture segments 22, 26 in a specific pattern. The heating array 82 has non-frangible leads 83 such that the heating array 82 is removed from between the suture segments 22, 26 after melting and prior to cooling and bonding of the suture segments 22, 26.

Figure 23:
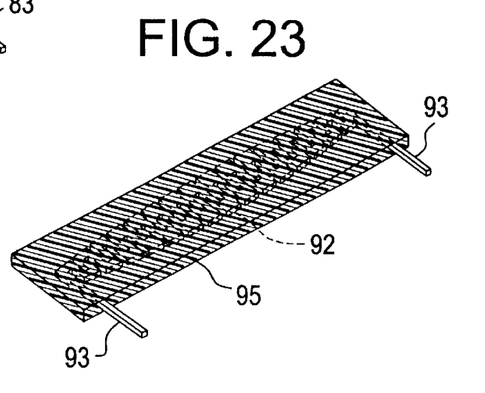
FIG. 23 is a perspective view of a non-uniform heating array encapsulated in plastic for use with a suture welder according to the present disclosure.

FIG. 23 is a perspective view of a non-uniform heating array 92, similar to the heating array 82 of FIG. 22, but encapsulated in plastic 95. The heating array 92 has frangible leads 93 such that the heating array 92 remains between the suture segments 22, 26 after melting and prior to cooling and bonding of the encapsulate 95 and the suture segments 22, 26.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description. All changes that come within the meaning and range of the equivalency of the claims are therefore intended to be embraced therein.

What is claimed is:

1. A suture welder comprising:
   a first jaw defining a first region for receiving a first suture segment;
   a second jaw defining a second region for receiving a second suture segment such that the first and the second suture segments overlap; and
   a heater element retractably positioned between said first region and said second region.

2. An endoscopic assembly including a suture welder according to claim 1, and further comprising:
   a handle;
   a controller mounted on the handle; and
   a stem operatively connecting the controller to the suture welder.

3. An endoscopic assembly according to claim 2, wherein the suture welder is removably attached to the stem.

4. An endoscopic assembly according to claim 2, wherein the suture welder and the stem are removably attached to the controller and the handle.

5. A suture welder according to claim 1, wherein the jaws are made of a low friction material.

6. A suture welder according to claim 1, wherein the jaws include suture grooves.

7. A suture welder according to claim 1, wherein the jaws include suture grooves having surfaces of low friction material.

8. A suture welder according to claim 1, wherein the jaws are pivotally connected together.

9. A suture welder according to claim 1, wherein the heater element comprises an electrical resistance heater element.

10. A suture welder according to claim 1, wherein the heater element comprises a film.

11. A suture welder according to claim 1, wherein the heater element comprises a film made of an alloy of nickel, chromium, and iron.

12. A suture welder according to claim 1, wherein the heating element comprises a wire.

13. A suture welder according to claim 1, wherein the heating element comprises a wire made of an alloy of nickel, chromium, and iron.

14. A suture welder according to claim 1, wherein the heater element is coated with a low friction material.

15. A suture welder according to claim 1, wherein the heater element is coated with polyamide film.

16. A suture welder according to claim 1, wherein a surface of the heater element is etched.

17. A suture welder according to claim 1, further comprising a withdrawal mechanism connected to the heater element and adapted to pull the heater element between the suture segments.

18. A suture welder according to claim 17, further comprising a release mechanism adapted to release the heater element after at least one of a predetermined time, a predetermined temperature, and other indicia that a suitable amount of melting of the suture segments has occurred.

19. A suture welder according to claim 1, wherein the jaws are adapted to come together no less than a predetermined minimum distance.

20. A suture welder according to claim 1, wherein the welder includes a sensor monitoring a distance between the jaws.

21. A suture welder according to claim 20, wherein the sensor is contact-less.

22. A suture welder according to claim 21, wherein the contact-less position sensor comprises a Hall effect cell including a sensor positioned in one of the jaws and a magnetic target positioned in the other of the jaws, and a circuit that provides an output signal indicative of a distance between the sensor and the magnetic target.

23. A suture welder according to claim 1, wherein the heater element has frangible leads extending therefrom.

24. A suture welder according to claim 1, wherein the heater element is encapsulated in material bondable wit suture material.

25. A suture welder according to claim 1, wherein the heater element comprises a non-uniform heating array.

26. A suture welder according to claim 1, further including a mechanism for biasing the jaws together.

27. A method of welding suture segments comprising:
   positioning suture segments in contact with opposite sides of a heater element;
   energizing the heater element such that surfaces of the suture segments in contact with the heater melt;
   moving the heater element between the suture segments;
   biasing the melted surfaces of the suture segments together;
   allowing the melted surfaces to cool and become fused; and
   releasing the fused suture segments.

28. A method according to claim 27, wherein the suture segments are fused such that the fused suture segments include a fused layer between and joining the first and the second suture segments.

29. A method according to claim 27, wherein the suture segments are fused such that the fused suture segments include a fused layer between and joining the first and the second suture segments, and the fused layer includes fused material from both the first and the second suture segments, the fused layer is relatively thin in comparison to each of the first and the second suture segments, and the fused layer has a relatively large shear area.

30. A method according to claim 27, wherein contact between the suture segments is maximized.

31. A method according to claim 27, further comprising threading the suture segments into suture grooves of the jaws on opposite sides of the heater element prior to energizing the heater element.

32. A method according to claim 27, wherein the heater element is energized with an electrical current.

33. A method according to claim 27, wherein the heater element is removed from between the suture segments after at least one of a predetermined time, a predetermined temperature, and other indicia that a suitable amount of melting of the suture segments has occurred.

34. A method according to claim 27, wherein the heater element is pulled between the suture segments.

35. A method according to claim 27, wherein at least a portion of the heater element is allowed to remain in the fused suture segments.

36. A method according to claim 27, wherein the heater element is energized in a non-uniform manner.

37. A method according to claim 27, wherein the method is conducted endoscopically.

38. A suture welder comprising:
   a first jaw for receiving a first suture segment;
   a second jaw for receiving a second suture segment, said second jaw being pivotally connected to said first jaw;
   a heater element being positionable and retractable along an axis between said first jaw and said second jaw.

39. An endoscopic assembly including a suture welder according to claim 38, and further comprising:
   a handle;
   a controller mounted on the handle; and
   a stem operatively connecting the controller to the suture welder.

40. An endoscopic assembly according to claim 39, wherein the suture welder is removably attached to the stem.

41. An endoscopic assembly according to claim 39, wherein the suture welder and the stem are removably attached to the controller and the handle.

42. A suture welder according to claim 38, wherein the jaws are made of a low friction material.

43. A suture welder according to claim 38, wherein the jaws include suture grooves.

44. A suture welder according to claim 38, wherein the jaws include suture grooves having surfaces of low friction material.

45. A suture welder according to claim 38, wherein the heater element comprises an electrical resistance heater element.

46. A suture welder according to claim 38, wherein the heater element comprises a film.

47. A suture welder according to claim 39, wherein the heater element comprises a film made of an alloy of nickel, chromium, and iron.

48. A suture welder according to claim 38, wherein the heating element comprises a wire.

49. A suture welder according to claim 38, wherein the heating element comprises a wire made of an alloy of nickel, chromium, and iron.

50. A suture welder according to claim 38, wherein the heater element is coated with a low friction material.

51. A suture welder according to claim 38, wherein the heater element is coated with polyamide film.

52. A suture welder according to claim 38, wherein a surface of the heater element is etched.

53. A suture welder according to claim 38, further comprising a withdrawal mechanism connected to the heater element and adapted to pull the heater element between the suture segments.

54. A suture welder according to claim 53, further comprising a release mechanism adapted to release the heater element after at least one of a predetermined time, a predetermined temperature, and other indicia that a suitable amount of melting of the suture segments has occurred.

55. A suture welder according to claim 38, wherein the jaws are adapted to come together no less than a predetermined minimum distance.

56. A suture welder according to claim 38, wherein the device includes a sensor monitoring a distance between the jaws.

57. A suture welder according to claim 56, wherein the sensor is contact-less.

58. A suture welder according to claim 57, wherein the contact-less position sensor comprises a Hall effect cell including a sensor positioned in one of the jaws and a magnetic target positioned in the other of the jaws, and a circuit that provides an output signal indicative of a distance between the sensor and the magnetic target.

59. A suture welder according to claim 38, wherein the heater element has frangible leads extending therefrom.

60. A suture welder according to claim 38, wherein the heater element is encapsulated in material bondable with suture material.

61. A suture welder according to claim 38, wherein the heater element comprises a non-uniform heating array.

62. A suture welder according to claim 38, further including a mechanism for biasing the jaws together.

* * * * *